(12) United States Patent
Wada et al.

(10) Patent No.: US 8,728,780 B2
(45) Date of Patent: May 20, 2014

(54) PROCESS FOR PRODUCING HYDROXYCARBOXYLIC ACID

(75) Inventors: Mitsufumi Wada, Mobara (JP); Daisuke Mochizuki, Mobara (JP); Hitoshi Takahashi, Chiba (JP); Takashi Morishige, Mobara (JP); Katsuyuki Takahashi, Chiba (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 927 days.

(21) Appl. No.: 11/587,806

(22) PCT Filed: Apr. 19, 2005

(86) PCT No.: PCT/JP2005/007416
§ 371 (c)(1),
(2), (4) Date: Oct. 27, 2006

(87) PCT Pub. No.: WO2005/106005
PCT Pub. Date: Nov. 10, 2005

(65) Prior Publication Data
US 2008/0032370 A1 Feb. 7, 2008

(30) Foreign Application Priority Data
Apr. 27, 2004 (JP) ................................ 2004-131352

(51) Int. Cl.
C12P 7/42 (2006.01)

(52) U.S. Cl.
USPC ....................................................... 435/146

(58) Field of Classification Search
None
See application file for complete search history.

(56) References Cited

U.S. PATENT DOCUMENTS

| 4,876,197 A * | 10/1989 | Burke et al. | 435/320.1 |
| 2002/0164729 A1 | 11/2002 | Skraly et al. | |

FOREIGN PATENT DOCUMENTS

| JP | 54-119089 A | 9/1979 |
| JP | 59-85296 A | 5/1984 |
| JP | 01-168292 A | 7/1989 |
| JP | 5-331100 A | 12/1993 |
| JP | 08-084592 A | 4/1996 |
| JP | 10-174593 A | 6/1998 |
| JP | 10-174594 A | 6/1998 |
| WO | WO 02/08428 A2 | 1/2002 |

OTHER PUBLICATIONS

Kataoka, Michihiko et al., "Glycolic Acid Production Using Ethylene Glycol-Oxidizing Microorganisms", Bioscience, Biotechnology, and Biochemistry, Oct. 2001, pp. 2265-2270, vol. 65, Japan Society for Bioscience, Biotechnology, and Agrochemistry.
Boronat, Albert et al., "Experimental Evolution of a Metabolic Pathway for Ethylene Glycol Utilization by *Escherichia coli*", Journal of Bacteriology, Jan. 1983, pp. 134-139, vol. 153, No. 1, American Society for Microbiology.
Boronat, Albert, et al., "Experimental Evolution of Propanediol Oxidoreductase in *Escherichia coli*", Biochimica et Biophysica Acta (G), Jan. 7, 1981, pp. 98-107, vol. 672, No. 1, Elsevier/North-Holland Biomedical Press.
Bruce Alberts et al. "*Molecular Biology of The Cell*," 84-85 (1983).
Supplementary European Search Report mailed Nov. 3, 2010, for Application No. 05731957.6.-1521/1746076 PCT/JP2005007416.
Aklani-Rose G. Delacruz-Hidalgo et al. "*Biochemical and applied studies of microbial oxidoreductaes*" 2(1) Institute for Chemical Research, Kyoto University Retrieved from the Internet: www.kuicr.kyoto-u.ac.jp/labos/6m2/oubikyo/2004060106.pdf [retrieved on Oct. 19, 2010], 39-46 (Jun. 2004).
Jianfeng Jin et al. "The Expression of Spinach Glycolate Oxidase (GO) in E. coli and the Application of GO in the Production of Glyoxylic Acid," 25 Molecular Biotechnology 207-214 (2003).
M. Felisa Núñez et al. "The gene yghK linked to the glc operon of *Escherichia coli* encodes a permease for glycolate that is structurally and functionally similar to L-lactate permease," 147 Microbiology 1069-1077 (2001).
S. Varenne et al. "A Mutant of *Escherichia coli* Deficient in Pyruvate Formate Lyase," 141 Molec. Gen. Genet. 181-184 (1975).
Chen et al., "Constitutive Activation of the *fucAO* Operon and Silencing of the Divergently Transcribed *fukPIK* Operon by an IS5 Element in *Escherichia coli* Mutants Selected for Growth on L-1,2-Propanedlol," Journal of Bacteriology, Nov. 1989, vol. 173, No. 11, pp. 6097-6105, American Society for Microbiology.
Hidalgo et al., "Molecular Cloning and DNA Sequencing of the *Escherichia coli* K-12 ald Gene Encoding Aldehyde Dehydrogenase," Journal of Bacteriology, Oct. 1991, vol. 173, No. 19, pp. 6118-6123, American Society for Microbiology.
Caballero et al., "Identification of Lactaldehyde Dehydrogenase and Glycolaldehyde Dehydrogenase As Functions of the Same Protein in *Escherichia coli*," The Journal of Biological Chemistry, 1983, vol. 258, No. 12, pp. 7788-7792.
Pellicer et al., "glc Locus of *Escherichia coli*: Characterization of Genes Encoding the Subunits of Glycolate Oxidase and glc Regulator Protein," Journal of Bacteriology, Apr. 1996, vol. 178, No. 7, pp. 2051-2059, American Society for Microbiology.
Rodel et al., "Primary structures of *Escherichla coli* pyruvate formate-lyase and pyruvate-formate-lyase-activating enzyme deduced from the DNA nucleotide sequences," Eur. J. Biochem., 1988, vol. 177, pp. 153-158.

* cited by examiner

*Primary Examiner* — Tekchand Saidha
*Assistant Examiner* — Younus Meah
(74) *Attorney, Agent, or Firm* — Buchanan Ingersoll & Rooney PC (57) ABSTRACT

An object of the invention is to produce a microorganism which yields high amounts in a short time of a hydroxycarboxylic acid reduced in impurity content. This invention further provides a process for producing a hydroxycarboxylic acid, including glycolic acid, using the microorganism. This process enables a hydroxycarboxylic acid having high purity to be supplied at low cost.

10 Claims, 2 Drawing Sheets

Fig. 1

Reaction Time (hr)

Fig. 2

Culture Time (hr) after initiating addition of ethylene glycol

SEQUENCE LISTING

```
<160> NUMBER OF SEQ ID NOS: 23

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgaattccgg agaaagtctt atgatggcta acagaatgat tctg                         44

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgaagcttg catttaccag gcggtatgg                                          29

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aacgaattct cgcaatgatt gacacgattc                                         30
```

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acagaattcg ctatttgtta gtgaataaaa gg                                32

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gctctagacg gagaaagtct tatgatggct aacagaatga ttctg                  45

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgaattccgg agaaagtctt atgtcagtac ccgttcaaca tcc                    43

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gctctagact ctttcactca ttaagactg                                    29

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tactgcagtg atccttgcag gcaatgc                                      27

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggtctagaat catcagagag acggaatcg                                    29

```
<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtctagaat gagtgaaaga ggcggag                                              27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaggtaccga tgctggtgcg aagaagg                                              27

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gctctagacc ttctccttgt tgctttacg                                            29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aactgcagag agaggtagct aatggaacg                                            29

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtctagagc aatgattgac acgattcg                                             28

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
caggtaccat ccttatcacc agcaacc                                              27

<210> SEQ ID NO 16
<211> LENGTH: 27
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttggtaccgt tctgccagca actgacg                                           27

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtctagagt acctctgtgc gtcactgg                                          28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctctagacg ctttgttgtg ttgtgtgg                                          28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aactgcagga tcggtcaatg attgcagc                                          28

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcacgaaagc tttgattacg                                                   20

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttattgcatg cttagatttg actgaaatcg                                        30

<210> SEQ ID NO 22
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 22
ttattgcatg cttatttact gcgtacttcg                                          30

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaggcctacg aaaagctgca g                                                   21
```

PROCESS FOR PRODUCING HYDROXYCARBOXYLIC ACID

TECHNICAL FIELD

The present invention relates to a microorganism which produces a hydroxycarboxylic acid including glycolic acid and a process for producing the hydroxycarboxylic acid including glycolic acid using the same.

BACKGROUND ART

Since some substances belonging to hydroxycarboxylic acids are useful as a raw material for polymers or an intermediate for medicines, a process for effectively producing such substances have been in demand.

As an example, glycolic acid (α-hydroxyacetic acid) can be cited. Glycolic acid has been used as a cleaning agent or a raw material for cosmetics, but has recently been paid attention to as a raw material of polyglycolic acid which is useful as a gas barrier polymer or a medical polymer. The reason why glycolic acid has been paid attention to as a gas barrier material is that the layer of polyglycolic acid has the property of a high oxygen barrier and is provided with performance as a material for packing food or carbonated beverage which goes easily bad in the presence of oxygen.

In order to actually produce polyglycolic acids on the industrial scale in the future, glycolic acid that is its raw material must be supplied in high purity and at low cost. However, glycolic acid of a chemically synthesized product which is currently available from the market contains not a few impurity contents, so there is a problem as a raw material for polymers in terms of purity. It is because these impurity contents not only prevent a dehydrative condensation reaction of glycolic acid, but also methoxy acetate that is one of these impurity contents is a compound suspicious of carcinogenic potential. Therefore, it is not desirable that such impurity contents are included in a packing material for food or beverage. Of course, it is technically possible to remove impurity contents by purification, but such purified products actually involve high cost. Thus, such purified products are not realistic as a raw material for packing at low cost.

In order to avoid the aforementioned problem shown in glycolic acid of the chemically synthesized product, production of glycolic acid using ethylene glycol (hereinafter may be referred to as EG) as a raw material has been attempted according to the biological method. In Japanese Patent Laid-open Nos. H10-174593 (1998-174593) and H10-174594 (1998-174594), there has been disclosed a method for producing glycolic acid by a microorganism, which comprises culturing yeast belonging to *Pichia* (genus), *Rhodotorula* (genus), *Sporobolomyces* (genus), *Kluyveromyces* (genus) or *Torulopsis* (genus), a strain belonging to *Nocardia* (genus), a strain belonging to *Rhodococcus* (genus), or an *Escherichia coli* B strain in a medium containing ethylene glycol for separating and collecting glycolic acid from the culture broth. Incidentally, there has been disclosed that the yield of glycolic acid is low relative to *Escherichia coli* K12 strain. Of the methods for producing glycolic acid as described in Examples of Japanese Patent Laid-open Nos. H10-174593 (1998-174593) and H10-174594 (1998-174594), a method comprising employing *Pichia naganishii* results in the highest accumulation concentration of glycolic acid, obtaining 35.3 g/L of glycolic acid in a reaction for 30 hours. The production of glycolic acid employing *Pichia naganishii* has been reported in a literature (Kataoka, M., et al., Biosci. Biotechnol. Biochem., Vol. 65 (10) pp. 2265-2270 (2001)) that 105 g/L of glycolic acid is obtained by a reaction for 120 hours due to further improvement in the reaction conditions. In short, in a method for producing glycolic acid employing *Pichia naganishii*, the time required for a reaction from ethylene glycol to glycolic acid is long, that is 120 hours, which causes an increase in the production cost of glycolic acid. So, the reaction time has been required to be reduced when the actual production on the industrial scale is supposed. And there has been a problem such that, in this production method, by-product organic acids produced by a microorganism in use are entrained, thus causing difficulties in a purification process or a dehydrative condensation reaction thereafter.

Regarding a metabolic reaction from ethylene glycol to glycolic acid by a microorganism, the results of study using *Escherichia coli* conducted by Boronat et al. have been disclosed (Boronat, A., et al., J. Bacteriol., Vol. 153 (1), pp. 134-139, (1983)), namely, a two-stage metabolic pathway including a reaction from ethylene glycol to glycolaldehyde and a reaction from glycolaldehyde to glycolic acid. Boronat et al. have paid attention to the fact that propanediol oxidoreductase (hereinafter may be referred to as PDO redox enzyme) of a catalytic enzyme of a reaction from 1,2-propanediol (hereinafter may be referred to as PDO) to lactaldehyde also recognizes ethylene glycol as a substrate (Boronat, A., et al., Biochim. Biophys. Acta, Vol. 672, pp. 98-107, (1981)). A strain which has the enhanced activity of glycolaldehyde dehydrogenase (hereinafter may be referred to as GAL dehydrogenase) of a catalytic enzyme of a reaction from glycolaldehyde to glycolic acid is isolated from strains in which activity of the PDO redox enzyme is enhanced by mutation. Incidentally, Table 1 below is cited from a thesis by Boronat et al.

TABLE 1

| Strains | Activity of PDO redox enzyme (U/mg protein) | Activity of GAL dehydrogenase (U/mg protein) | PDO utilizing capability | EG utilizing capability |
|---|---|---|---|---|
| G1 strain (referenced strain) | 0.005 | 0.145 | No | No |
| G3 strain | 0.130 | 0.165 | Yes | No |
| EG3 strain | 0.415 | 0.560 | (not mentioned) | Yes |

An *Escherichia coli* G1 strain of the referenced strain is able to utilize neither of 1,2-propanediol nor ethylene glycol. A G3 strain that is a mutant strain in which activity of the PDO redox enzyme is remarkably enhanced has acquired the PDO utilizing capability, but still cannot be able to utilize EG. On the basis of these results, Boronat et al. have reasoned that the reason why the G3 strain cannot be able to utilize EG might be that a reaction from glycolaldehyde to glycolic acid does not proceed due to insufficient activity of GAL dehydrogenase. They have concluded that their reasoning is right because a mutant EG3 strain in which activity of GAL dehydrogenase is remarkably enhanced is isolated, and this strain utilizes EG. In other words, Boronat et al. insist that activity of GAL dehydrogenase must be sufficient in order to produce glycolic acid from EG.

On the other hand, a new knowledge disclosed in the present specification is that enhancement of GAL dehydrogenase activity is not necessarily required in order to produce glycolic acid from EG, but only enhancement of activity of PDO redox enzyme may be sufficient. Such a difference is caused because Boronat et al. have only paid attention to enhancement of GAL dehydrogenase activity in the EG3 strain and have not paid attention to enhancement of activity of PDO redox enzyme as well at the same time. Considering the test results of Boronat et al. again based on our knowledge, the EG3 strain is able to acquire the EG utilizing capability not because activity of GAL dehydrogenase is enhanced, but because activity of PDO redox enzyme is enhanced.

Furthermore, according to a report by Boronat et al., in the EG3 strain, glycolaldehyde that is an intermediate is accumulated under the condition in the presence of glycolic acid along with EG as a substrate. Namely, this shows to cause troubles such that glycolaldehyde that is an intermediate is accumulated as impurity content when glycolic acid is produced from EG as a raw material according to the biological method using *Escherichia coli*.

According to the past knowledge from the aforementioned facts, it is shown that enhancement of activity of GAL dehydrogenase is absolutely necessary when glycolic acid is produced from EG using *Escherichia coli* and glycolaldehyde that is an intermediate is accumulated in the produced glycolic acid. From such a reason, even the skilled person in the art wasn't able to easily suppose that glycolic acid can be selectively produced without enhancement of GAL dehydrogenase activity and glycolic acid can be even produced with good efficiency without including glycolaldehyde of an intermediate.

Various investigations of methods for producing glyceric acid as example of hydroxycarboxylic acids besides glycolic acid have also been performed. In such investigations, as a method for producing glyceric acid using inexpensive glycerol as a raw material, a chemical synthesis method comprising using a Pt catalyst has been disclosed in Japanese Patent Laid-open No. H5-331100 (1993-331100) and a biological method by a microorganism belonging to *Gluconobacter* (genus) has been disclosed in Japanese Patent Laid-open No. H1-168292 (1989-168292). In the former method comprising using a Pt catalyst, the reaction selectivity of about 80% is never sufficient, thus generating by-products in a large amount and there is shown about a need to more strictly control the reaction temperature. In the latter biological method, a method for producing D-glyceric acid using glycerine as a raw material has been described, but there is a problem in that it takes a long time of 4 days required for the preparation of a microbial mass and the reaction and it is possible to easily suppose that a large amount of by-product organic acids derived from a microorganism in use are entrained into the prepared glyceric acid. By the way, there has not been known about a method for producing L-glyceric acid.

Furthermore, as an example of hydroxycarboxylic acid, a method for producing hydroxyethoxy acetate according to the biological method has been disclosed in Japanese Patent Laid-open No. S59-85296 (1984-85296). The method comprises culturing yeast belonging to *Candida* (genus), *Torulopsis* (genus), *Rhodotorula* (genus), *Hansenula* (genus), *Debaryomyces* (genus), *Cryptococcus* (genus) and *Pichia* (genus) in a medium containing diethylene glycol, separating and collecting hydroxyethoxy acetate from the culture broth. In this production method, it is shown that it takes a long time required for culturing and diglycolic acid in a large amount is also produced as a by-product. From the fact, it is easily imagined that great efforts for the separation and purification of hydroxyethoxy acetate are needed.

Patent Document 1: Japanese Patent Laid-open No. H10-174593 (1998-174593)
Patent Document 2: Japanese Patent Laid-open No. H10-174594 (1998-174594)
Patent Document 3: Japanese Patent Laid-open No. H5-331100 (1993-331100)
Patent Document 4: Japanese Patent Laid-open No. H1-168292 (1989-168292)
Patent Document 5: Japanese Patent Laid-open No. S59-85296 (1984-85296)
Non-patent Document 1: Kataoka, M., et al., Biosci. Biotechnol. Biochem., Vol. 65 (10), pp. 2265-2270, (2001)
Non-patent Document 2: Boronat, A., et al., J. Bacteriol., Vol. 153 (1), pp. 134-139, (1983)
Non-patent Document 3: Boronat, A., et al., Biochim. Biophys. Acta, Vol. 672, pp. 98-107, (1981)

DISCLOSURE OF THE INVENTION

As described above, various methods for producing a hydroxycarboxylic acid including glycolic acid in the past has drawbacks such that the hydroxycarboxylic acid obtained by the chemical synthesis method has generally low purity because of impurity content contained therein in a large amount, the productivity per unit hour of facilities becomes low because of the long reaction time in the biological method, thus increasing the production cost, and by-product organic acids are entrained. Under the above circumstances, an object of the present invention to solve is to supply hydroxycarboxylic acids including glycolic acid in a short time at low cost and in large quantities, and to enhance the purity by reducing by-products.

As an improvement plan to solve the above object, the present inventors have found that a process for producing glycolic acid from ethylene glycol is suitable for the object of the present invention by using a microorganism which has fully enhanced activity of the enzyme alone which is changed by a method comprising introducing a gene encoding an enzyme catalyzing a reaction from ethylene glycol to glycolaldehyde in the form of plasmid or the like as a substitute of a microorganism selected from the natural system which has been used for the production of glycolic acid according to the biological method in the past. And the present inventors have found a desired effect that cannot be expected to be able to reduce the amount of glucose necessary for the culture of a microbial mass by using a microorganism in which activity of an enzyme catalyzing a reaction from ethylene glycol to glycolaldehyde and activity of an enzyme catalyzing a reaction from glycolaldehyde to glycolic acid are enhanced by introducing a gene encoding the two enzymes in the form of plasmid as compared to a microorganism in which only activity of an enzyme catalyzing a reaction from ethylene glycol to glycolaldehyde is enhanced. In addition, the present inventors have found that the aforementioned microorganism is capable of producing glycolic acid with much higher purity (small amount of by-product organic acids) because by-product organic acids such as oxalic acid or acetic acid can be decreased by reducing activity of an enzyme catalyzing a reaction from glycolic acid to glyoxilic acid and/or activity of an enzyme catalyzing a reaction from pyruvic acid to formic acid. The present inventors have also found that a situation in a cell becomes more suitable for the production of glycolic acid by the reduction in activity of these two enzymes so that the productivity of glycolic acid is considerably improved, though details are not clear. Furthermore, the present inventors have found these microorganisms can be also used for a method for producing hydroxycarboxylic acids in addition to glycolic acid.

That is, the present invention is specified by the following matters from [1] to [9]:

[1] a process for producing hydroxycarboxylic acids with aliphatic polyhydric alcohols having a hydroxyl group at the end as a substrate, which comprises using a microorganism which has the imparted or enhanced activity of an enzyme catalyzing a reaction from ethylene glycol to glycolaldehyde;

[2] the production process as set forth in [1], which comprises imparting or enhancing activity of the enzyme of the microorganism by introducing a gene encoding the enzyme as set forth in [1] in the form of plasmid;

[3] a process for producing hydroxycarboxylic acids with aliphatic polyhydric alcohols having a hydroxyl group at the end as a substrate, which comprises using a microorganism which has the imparted or enhanced activity of both an enzyme catalyzing a reaction from ethylene glycol to glycolaldehyde and an enzyme catalyzing a reaction from glycolaldehyde to glycolic acid by introducing a gene encoding the two enzymes in the form of plasmid;

[4] the production process as set forth in [2] or [3], which comprises using a microorganism expressing the enzyme by functionally linking a gene encoding an enzyme catalyzing a reaction from ethylene glycol to glycolaldehyde and/or a gene encoding an enzyme catalyzing a reaction from glycolaldehyde to glycolic acid to a promoter of the gene which controls expression of a protein involved in a glycolytic pathway, a nucleic acid biosynthesis pathway or an amino acid biosynthesis pathway;

[5] the production process as set forth in any one of [1] to [4], in which the enzyme catalyzing a reaction from ethylene glycol to glycolaldehyde is lactaldehyde reductase, and the enzyme catalyzing a reaction from glycolaldehyde to glycolic acid is lactaldehyde dehydrogenase;

[6] the production process as set forth in any one of [1] to [5], which comprises using a microorganism in which activity of glycolate oxidase inherent in the microorganism is inactivated or decreased, and/or activity of pyruvate formate-lyase is inactivated or decreased;

[7] the production process as set forth in any one of [1] to [6], in which the hydroxycarboxylic acid is a hydroxycarboxylic acid having optical activity;

[8] a microorganism used for the production process as set forth in any one of [1] to [7]; and

[9] an aqueous solution of glycolic acid obtained by using ethylene glycol as set forth in [6] as a substrate with the yield of not less than 95% and the production rate of not less than 2 g/L/hr.

Effect of the Invention

Since a microorganism which highly yields glycolic acid reduced impurity content in a much shorter time than the ones known up to now according to the present invention is produced, glycolic acid having high purity which can be used as a raw material for polymers can be industrially produced at low cost. Furthermore, by applying the aforementioned production process, hydroxycarboxylic acids can also be produced in addition to glycolic acid.

Meanwhile, since glycolic acid can be highly produced with only one target enzyme in which its activity must be enhanced, which is contrary to the known information on the production of glycolic acid, efforts required for enhancement of activity of the enzymes can be reduced, and at the same time, undesired adverse effects on a host microorganism such as dropout of the introduced gene due to stresses caused by artificially enhancing activity of a plurality of enzymes can be avoided.

Furthermore, by reducing glucose necessary for the culture of a microorganism to be supplied for the production of hydroxycarboxylic acids, a method which reduces the production cost is provided.

BEST MODE FOR CARRYING OUT THE INVENTION

The present invention will be described in more detail below.

In the present invention, the enzyme catalyzing a reaction from ethylene glycol to glycolaldehyde is not particularly limited as far as it is an enzyme capable of producing glycolaldehyde using ethylene glycol as a reaction substrate, and indicates all of such enzymes. As such an enzyme, lactaldehyde reductase can be cited.

In the present invention, the microorganism which has the imparted activity of a certain target enzyme refers to a microorganism which has not activity of the enzyme at all, but which is provided with activity of the enzyme according to any method. In the present invention, the microorganism which has the enhanced activity of a certain target enzyme refers to a microorganism in which activity of the enzyme is considerably enhanced as compared to the wild type microorganism. These microorganisms can be produced, for example, by using a method of introducing a gene encoding the enzyme into a wild type microorganism (or a microorganism before recombination) using a gene recombination technique or the like. As a method for introducing the gene into the wild type microorganism (or a microorganism before recombination), a method for introducing the gene into the microorganism in the form of plasmid can be cited. Preparation of the genome DNA used for introduction of a gene into a microorganism, preparation of plasmid, digestion and ligation of DNA, transformation, PCR (Polymerase Chain Reaction), design and synthesis of oligonucleotide used as a primer and the like can be carried out according to a usual method well known to the skilled person in the art. These methods have been disclosed in Sambrook, J., et al., "Molecular Cloning A Laboratory Manual, Second Edition", Cold-Spring Harbor Laboratory Press, (1989) and the like.

The microorganism in the present invention refers to a generic name of a microorganism capable of having a capability to produce a hydroxycarboxylic acid from aliphatic polyhydric alcohol having a hydroxyl group at the end by using any means regardless of whether it inherently has a capability to produce a hydroxycarboxylic acid from aliphatic polyhydric alcohol having a hydroxyl group at the end. As such a microorganism, *Escherichia coli* can be cited.

In the present invention, the aliphatic polyhydric alcohol having a hydroxyl group at the end has a hydroxyl group at the end of a carbon chain and is an aliphatic compound having two or more hydroxyl groups in the molecule. In such a case, its structure is not particularly limited. Examples of such a compound include ethylene glycol, diethylene glycol, triethylene glycol, tetraethylene glycol, glycerol, 1,3-propanediol, 1,2-butanediol, 1,3-butanediol, 1,4-butanediol, 1,2,4-butanetriol and the like.

"In the form of plasmid" when introducing a gene encoding a certain target enzyme into a microorganism in the present invention refers to preparation of a recombinant plasmid by linking the gene to a vector and introduction of the prepared plasmid into the microorganism by a method of transformation or the like. Also, when the desired gene is functionally linked to a strong promoter constantly functioning in a microorganism as described in Examples of the present invention, it is possible to achieve the object of the present invention by using a plasmid in which the number of copies per microorganism cell is generally said to be low because of a property of replicon in a plasmid. As the plasmid having such a replicon, pACYC184 (GenBank accession number: X06403) and the like can be cited.

The enzyme catalyzing a reaction from glycolaldehyde to glycolic acid in the present invention is not particularly limited as far as it is an enzyme capable of producing glycolic acid using glycolaldehyde as a reaction substrate, and indicates all such enzymes. As such an enzyme, lactaldehyde dehydrogenase can be cited.

In the present invention, the promoter of the gene which controls expression of the protein involved in the glycolytic pathway, the nucleic acid biosynthesis pathway or the amino acid biosynthesis pathway refers to a strong promoter which constantly functions in a microorganism, and is less susceptible to suppression of expression even in the presence of glucose. Specific examples thereof include a promoter of glyceraldehyde 3-phosphate dehydrogenase (hereinafter may be referred to as GAPDH) or a promoter of serine hydroxymethyl transferase.

The promoter in the present invention refers to a site, to which RNA polymerase having a sigma factor is bound and initiates transcription. For example, GAPDH promoter derived from an *Escherichia coli* is recorded in Base Nos. 397 to 440 in the base sequence information of GenBank accession number X02662.

In the present invention, the gene functionally linked to the promoter refers to a state that the gene is under control of promoter and the gene is bound to the promoter such that expression of the gene is proceeded by control of the promoter.

The lactaldehyde reductase in the present invention is classified into the enzyme number 1.1.1.77, based on the report of the enzyme committee of International Union of Biochemistry (I.U.B.), and refers to a generic name of an enzyme which reversibly catalyzes a reaction to produce lactaldehyde from 1,2-propanediol in the presence of oxidized nicotinamide adenine dinucleotide which is a coenzyme.

The lactaldehyde dehydrogenase in the present invention is classified into the enzyme number 1.2.1.22, based on the report of the enzyme committee of International Union of Biochemistry (I.U.B.), and refers to a generic name of an enzyme that catalyzes a reaction to produce lactic acid from lactaldehyde in the presence of oxidized nicotinamide adenine dinucleotide which is a coenzyme. It is also classified into the enzyme number 1.2.1.21, based on the report of the enzyme committee of International Union of Biochemistry (I.U.B.), and refers to a generic name of an enzyme glycolaldehyde dehydrogenase that catalyzes a reaction to produce glycolic acid from glycolaldehyde in the presence of oxidized nicotinamide adenine dinucleotide which is a coenzyme. This is because, in the prior literature using *Escherichia coli*, there has been reported that lactaldehyde dehydrogenase and glycolaldehyde dehydrogenase are the same enzyme (Caballero, E., et al., J. Biol. Chem., Vol. 258 (12), pp. 7788-7792 (1983)).

Gglycolate oxidase (hereinafter may be referred to as glcDEF) in the present invention is classified into the enzyme number 1.1.3.15, based on the report of the enzyme committee of International Union of Biochemistry (I.U.B.), and refers to a generic name of an enzyme which reversibly catalyzes a reaction to produce glyoxilic acid from glycolic acid.

Pyruvate formate-lyase (hereinafter may be referred to as pflB) in the present invention is classified into the enzyme number 2.3.1.54, based on the report of the enzyme committee of International Union of Biochemistry (I.U.B.), and refers to a generic name of an enzyme which reversibly catalyzes a reaction to produce formic acid from pyruvic acid.

Inactivation of functions of an enzyme glcDEF or pflB in the present invention means complete loss of activity of the enzyme. Decrease in functions of an enzyme glcDEF or pflB in the present invention means partial loss of activity of the enzyme. In order to inactivate or decrease functions of the enzyme, there are methods such as introducing a mutation into the gene encoding the protein, eliminating the gene, adding a drug which specifically inactivates the enzyme, irradiating the enzyme with ultraviolet rays or the like. Specifically, an *Escherichia coli* MT-11023 strain can be cited as a microorganism in which functions of these enzymes are inactivated by disruption of glcDEF gene and pflB gene.

Since the *Escherichia coli* MT-11023 strain is a strain in which glcDEF and pflB are inactivated by gene disruption, the present invention can be carried out easily using this strain. The present strain has been deposited on Mar. 10, 2005 as the deposition number FERM BP-10293 at International Patent Organism Depositary Center, Tsukuba Central 6, 1-1-1 Higashi, Tsukuba, Ibaraki, of National Institute of Advanced Industrial Science and Technology, based on the Budapest Treaty on the International Recognition of the Deposit of Microorganisms for the Purposes of Patent Procedure.

When carrying out the production process of the present invention, a microorganism microbial mass in a necessary amount is obtained usually by culturing and growing a microorganism which has the imparted or enhanced activity of an enzyme catalyzing a reaction from ethylene glycol to glycolaldehyde using a medium.

The medium to be used for the culture according to the present invention is not particularly limited if it is a medium containing carbon source, nitrogen source, inorganic ion and as needed traces of other organic components. As carbon source, saccharides such as glucose, fructose, molasses and the like; organic acids such as fumaric acid, citric acid, succinic acid and the like; and alcohols such as methanol, ethanol, glycerol and the like are properly used. As nitrogen source, inorganic nitrogen sources such as organic ammonium salts, inorganic ammonium salts, ammonia gas, ammonia water and the like; and organic nitrogen sources such as protein hydrolysates and the like are properly used. As inorganic ion, magnesium ion, phosphate ion, potassium ion, iron ion, manganese ion and others are properly used as required. As traces of organic components, vitamin, amino acid or the like and yeast extracts containing vitamin, amino acid or the like, peptone, corn steep liquor, casein hydrolysate and the like are properly used.

Incidentally, as the medium to be used for the culture according to the present invention, preferably used is a liquid medium considering that a microorganism is provided for the industrial production.

When the microorganism is cultured according to the present invention, the culture condition is not particularly limited. For example, when the microorganism is cultured while properly controlling pH and temperature in a pH range of 6 to 8, a temperature range of 25 to 40 degree centigrade under aerobic conditions, the time required for the culture is within 50 hours.

The reaction solution to be used for a reaction to produce hydroxycarboxylic acids according to the present invention is not particularly limited if it is a solution capable of adding (or containing) aliphatic polyhydric alcohol having a hydroxyl group at the end to be a substrate. Examples thereof include a buffer solution such as a potassium phosphate buffer solution and the like or a medium used for the culture of the aforementioned microorganism and pure water. In the present invention, a reaction is carried out by bringing the microorganism microbial mass previously obtained by the culture into contact with this solution. The microorganism microbial mass in use can be the culture broth itself wherein the culture is completed, or can be a microbial mass alone recovered from the culture broth, prior to use.

Upon the reaction in a process for producing hydroxycarboxylic acids of the present invention, the reaction condition is not particularly limited. But, for example, the reaction is preferably carried out while appropriately controlling pH and temperature in a pH range of 6 to 9, a temperature range of 20 to 40 degree centigrade.

A process for recovering a hydroxycarboxylic acid accumulated in the reaction solution obtained as described above is not particularly limited. But, there can be adopted, for example, a process comprising removing the microbial mass from the reaction solution by centrifugation or the like and then using a synthetic adsorbent resin, a process using a precipitant, a process comprising separating a hydroxycarboxylic acid according to other usual collection and separation methods.

EXAMPLES

Example 1

Construction of *Escherichia coli*-Derived Lactaldehyde Reductase Expression Vector and a Transformant of the Expression Vector The amino acid sequence and the base sequence of a gene (hereinafter may be simply referred to as fucO) of lactaldehyde reductase of *Escherichia coli* have been already reported (GenBank accession number: M31059). In order to acquire fucO, CGAATTCCGGAGAAAGTCTTATGATG-GCTAACAGAATGATTCTG (Sequence No. 1) and GTGAAGCTTGCATTTACCAGGCGGTATGG (Sequence No. 2) were used for a PCR amplification using the genome DNA of *Escherichia coli* MG1655 strain as a template, and the obtained DNA fragment was digested with restriction enzymes EcoRI and HindIII to give a fucO fragment of about 1.2 kbp. Furthermore, in order to acquire a glyceraldehyde 3-phosphate dehydrogenase (GAPDH) promoter, AAC-GAATTCTCGCAATGATTGACACGATTC (Sequence No. 3) and ACAGAATTCGCTATTTGTTAGTGAATAAAAGG (Sequence No. 4) were used for a PCR amplification using the genome DNA of *Escherichia coli* MG1655 strain as a template, and the obtained DNA fragment was digested with a restriction enzyme EcoRI to give a DNA fragment of about 100 bp which encodes a GAPDH promoter. The above-mentioned two DNA fragments were mixed with the fragment obtained by digestion of plasmid pUC18 with restriction enzymes EcoRI and HindIII, ligated using a ligase, and then transformed to an *Escherichia coli* DH5 strain, to give a transformant which grows on an LB agar plate containing 50 μg/mL of ampicillin. The obtained colony was cultured in an LB liquid medium containing 50 μg/mL of ampicillin at 37 degree centigrade overnight, and a plasmid pGAPfucO was recovered from the obtained microbial mass. This plasmid pGAPfucO was transformed to an *Escherichia coli* MG1655 strain, and cultured on an LB agar plate containing 50 μg/mL of ampicillin at 37 degree centigrade overnight to give a MG1655/pGAPfucO strain.

Incidentally, the *Escherichia coli* MG1655 strain and *Escherichia coli* DH5 strain can be obtained from American Type Culture Collection.

Example 2

Construction of Lactaldehyde Reductase and Lactaldehyde Dehydrogenase Double-Expression Vector and a Transformant of the Expression Vector The amino acid sequence and the base sequence of a gene (hereinafter may be simply referred to as fucO) of lactaldehyde reductase of *Escherichia coli* have been already reported (GenBank accession number: M31059). Furthermore, the amino acid sequence and the base sequence of a gene (hereinafter may be simply referred to as aldA) of lactaldehyde dehydrogenase of *Escherichia coli* have been already reported as well (GenBank accession number: M64541). In order to acquire fucO, GCTCTAGACG-GAGAAAGTCTTATGATGGCTAACAGAATGATTCTG (Sequence No. 5) and GTGAAGCTTGCATTTACCAG-GCGGTATGG (Sequence No. 2) were used for a PCR amplification using the genome DNA of *Escherichia coli* MG1655 strain as a template, and the obtained DNA fragment was digested with restriction enzymes XbaI and HindIII to give a fucO fragment of about 1.2 kbp. Furthermore, in order to acquire aldA, CGAATTCCGGAGAAAGTCTTATGTCAG-TACCCGTTCAACATCC (Sequence No. 6) and GCTCTA-GACTCTTTCACTCATTAAGACTG (Sequence No. 7) were used for a PCR amplification using the genome DNA of *Escherichia coli* MG1655 strain as a template, and the obtained DNA fragment was digested with restriction enzymes EcoRI and XbaI to give an aldA fragment of about 1.5 kbp. Furthermore, a fragment encoding a glyceraldehyde 3-phosphate dehydrogenase (GAPDH) promoter was obtained in the same manner as in Example 1. The above-mentioned three DNA fragments were mixed with the fragment obtained by digestion of plasmid pUC18 with restriction enzymes EcoRI and HindIII, ligated using a ligase, and then transformed to an *Escherichia coli* DH5 strain, to give a transformant which grows on an LB agar plate containing 50 μg/mL of ampicillin. The obtained colony was cultured in an LB liquid medium containing 50 μg/mL of ampicillin at 37 degree centigrade overnight, and a plasmid pGAPfucO-aldA was recovered from the obtained microbial mass. This plasmid pGAPfucO-aldA was transformed to an *Escherichia coli* MG1655 strain, and cultured on an LB agar plate containing 50 μg/mL of ampicillin at 37 degree centigrade overnight, to give a MG1655/pGAPfucO-aldA strain.

Example 3

Figure 1:
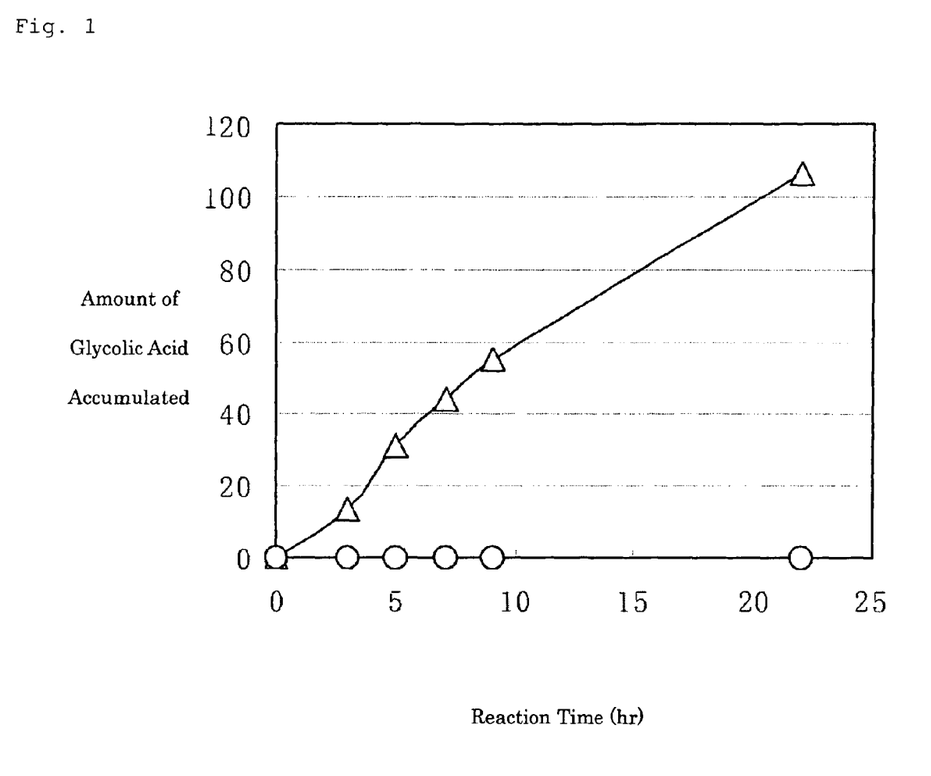
FIG. 1 is a graph which shows the time course of an amount of glycolic acid accumulated in the reaction solution in Example 3. In the figure, the triangle shows the results of *Escherichia coli* MG1655/pGAPfucO strain, while the circle shows the results of *Escherichia coli* MG1655 wild strain.

Production of Glycolic Acid by *Escherichia coli* MG1655/pGAPfucO Strain and *Escherichia coli* MG1655 Wild Strain The *Escherichia coli* MG1655/pGAPfucO strain obtained in Example 1 and *Escherichia coli* MG1655 wild strain were inoculated into 25 mL of LB Broth, Miller's culture solution (Difco244620) contained in a conical flask, and the culture was carried out with stirring overnight with 120 rpm at a culture temperature of 35 degree centigrade as preculture. Then, the whole amount of the respective preculture solutions was transferred to a 1 L-fermentor (BMJ-01, culture apparatus manufactured by ABLE Corporation) containing 475 g of the medium of the composition shown in Table 2 to carry out culture. The culture was carried out under the conditions including atmospheric pressure, an aeration rate of 1 vvm, a stirring speed of 800 rpm, a culture temperature of 35 degree centigrade and pH 7.2 (adjusted with an aqueous $NH_3$ solution). The microbial mass at 24 hours after starting the culture was collected by centrifugation (8,000 rpm for 20 minutes) and washed with pH 7.2 of 1 mM potassium phosphate buffer solution, and then suspended with this buffer solution to have 500 ml of final liquid amount. The suspension was transferred to a fermentor of a culture apparatus BMJ-01 manufactured by ABLE Corporation and ethylene glycol was added thereto at a rate of 5 g/hr to carry out the reaction for 22 hours. The reaction was carried out under the conditions including atmospheric pressure, an aeration rate of 1 vvm, a stirring speed of 800 rpm, a culture temperature of 35 degree centigrade and pH 7.2 (adjusted with an aqueous $NH_3$ solution). The amount of glycolic acid accumulated in the obtained reaction solution was measured by HPLC according to an established method. The results are shown in FIG. 1.

It was confirmed that 106 g/L of glycolic acid was accumulated in the *Escherichia coli* MG1655/pGAPfucO strain at 22 hours, while glycolaldehyde that is an intermediate from ethylene glycol to glycolic acid was not detected. On the other hand, in the wild strain, glycolic acid was not detected even after 22 hours of the reaction.

TABLE 2

| Medium Composition | |
|---|---|
| Polypepton | 7 g/L |
| Glucose | 30 g/L |
| $Fe_2SO_4$ | 0.09 g/L |
| $K_2HPO_4$ | 2 g/L |
| $KH_2PO_4$ | 2 g/L |
| $MgSO_4 \cdot 7H_2O$ | 2 g/L |
| $(NH_4)_2SO_4$ | 1.5 g/L |
| (Residue: Water) | |

Example 4

Figure 2:
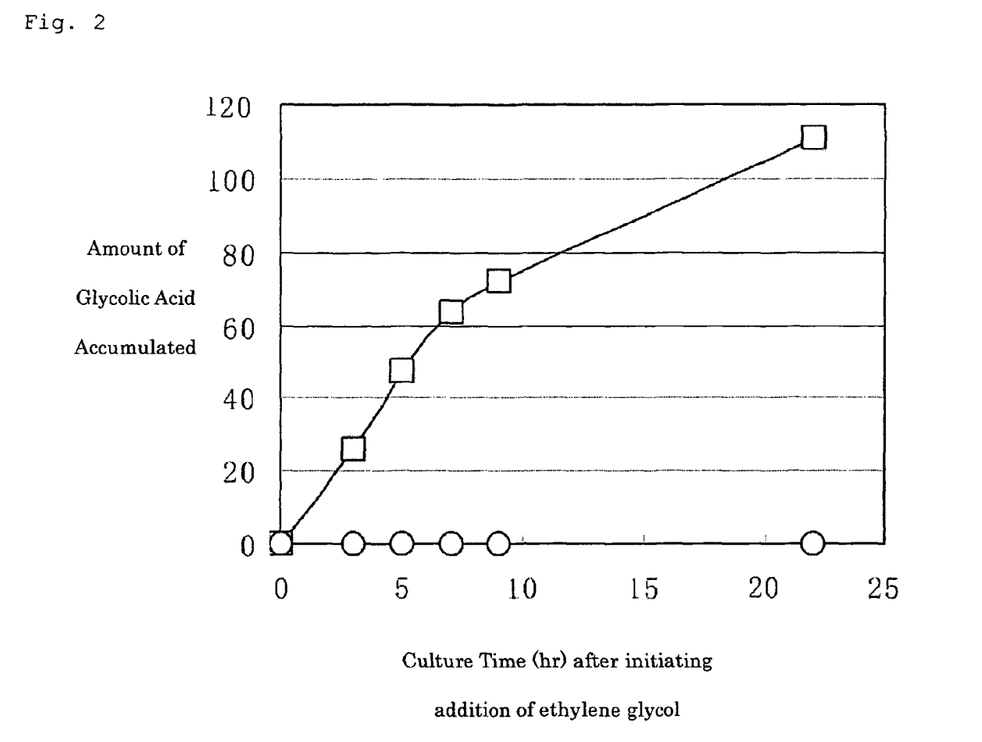
FIG. 2 is a graph which shows the time course of an amount of glycolic acid accumulated in the reaction solution in Example 4. In the figure, the square shows the results of *Escherichia coli* MG1655/pGAPfucO-aldA strain, while the circle shows the results of *Escherichia coli* MG1655 wild strain.

Production of Glycolic Acid by *Escherichia coli* MG1655/pGAPfucO-aldA Strain and *Escherichia coli* MG1655 Wild Strain The *Escherichia coli* MG1655/pGAPfucO-aldA strain obtained in Example 2 and *Escherichia coli* MG1655 wild strain were cultured in the same manner as in Example 3. After 24 hours from starting the culture, ethylene glycol was directly added to the fermentor in culture at a rate of 5 g/hr for 22 hours to carry out the reaction. The amount of glycolic acid accumulated in the obtained culture broth was measured by HPLC according to an established method. The results are shown in FIG. 2.

It was confirmed that, in the *Escherichia coli* MG1655/pGAPfucO-aldA strain, 110 g/L of glycolic acid was accumulated at 22 hours after starting the addition of ethylene glycol, while glycolaldehyde that is an intermediate from ethylene glycol to glycolic acid was not detected. On the other hand, in the wild strain, glycolic acid was not detected even at 22 hours after initiating the addition of ethylene glycol.

Example 5

Preparation of *Escherichia coli* MG1655aldA-Deleted Strain

The entire base sequence of the genome DNA of *Escherichia coli* is known (GenBank accession number: U00096), and the amino acid sequence and the base sequence of a gene (hereinafter may be simply referred to as aldA) of lactaldehyde dehydrogenase of *Escherichia coli* have also been reported (GenBank accession number: M64541). PCR was performed using the primer pair of TACTGCAGTGATCCT-TGCAGGCAATGC (Sequence No. 8) and GGTCTAGAAT-CATCAGAGAGACGGAATCG (Sequence No. 9), or the pair of GGTCTAGAATGAGTGAAAGAGGCGGAG (Sequence No. 10) and AAGGTACCGATGCTGGTGCGAA-GAAGG (Sequence No. 11), which were prepared on the basis of the gene information of aldA-adjacent region of the genome DNA of *Escherichia coli* MG1655 strain. Each of the obtained DNA fragments was digested with restriction enzymes PstI and XbaI, and XbaI and KpnI, to give fragments of about 800 bp and 700 bp respectively. These DNA fragments were mixed with the fragment obtained by digestion of a temperature-sensitive cloning vector pTH18cs1 (GenBank accession number: AB019610) [Hashimoto-Gotoh, T., Gene, Vol. 241, pp. 185-191 (2000)] with PstI and KpnI, ligated using a ligase, and then transformed to a DH5 strain at 30 degree centigrade, to give a transformant which grows on an LB agar plate containing 10 μg/ml of chloramphenicol. The obtained colony was cultured in an LB liquid medium containing 10 μg/ml of chloramphenicol at 30 degree centigrade overnight, and a plasmid was recovered from the obtained microbial mass.

This plasmid was transformed to an *Escherichia coli* MG1655 strain at 30 degree centigrade, and cultured on an LB agar plate containing 10 μg/ml of chloramphenicol at 30 degree centigrade overnight to give a transformant. The obtained transformant was applied onto an LB liquid medium containing 10 μg/ml of chloramphenicol and cultured at 30 degree centigrade overnight. Next, in order to obtain the cultured microbial mass, the cultured microbial mass was applied onto an LB agar plate containing 10 μg/ml of chloramphenicol to give colonies which grow at 42 degree centigrade. The obtained colonies were cultured in an LB liquid medium without containing an antibiotic at 30 degree centigrade overnight and further applied onto an LB agar plate without containing an antibiotic, to give colonies which grow at 42 degree centigrade.

From the grown colonies, 100 colonies were picked up randomly, and each of them was grown on an LB agar plate without containing an antibiotic and an LB agar plate containing 10 μg/ml of chloramphenicol, to select chloramphenicol-sensitive clones which grow only on an LB agar plate without containing an antibiotic. Furthermore, a fragment of about 3.2 kb containing aldA was amplified by PCR using the chromosome DNA of these desired clones to select a strain in which aldA was deleted, and the obtained strain was named as a MG1655aldA-deleted strain (hereinafter may be simply referred to as ΔaldA).

Example 6

Construction of ΔaldA/pGAPfucO Strain

The plasmid pGAPfucO obtained in Example 1 was transformed to the ΔaldA strain obtained in Example 5 and cultured on an LB agar plate containing 50 µg/mL of ampicillin at 37 degree centigrade overnight, to give a ΔaldA/pGAPfucO strain.

Example 7

Production of Glycolic Acid by ΔaldA/pGAPfucO Strain

Each of ΔaldA/pGAPfucO strain and MG1655/pGAPfucO strain was cultured, collected and washed in the same manner as in Example 3, and then ethylene glycol was added to the obtained microbial mass in the same manner as in Example 3 to carry out the reaction for 10 hours. It was confirmed that 64.8 g of glycolic acid was accumulated in the ΔaldA/pGAPfucO strain and 64.2 g of glycolic acid was accumulated in the MG1655/pGAPfucO strain by the reaction. It was shown that lactaldehyde dehydrogenase was not necessarily required for the production of glycolic acid.

Example 8

Comparison of Microbial Mass Growth of Escherichia coli MG1655/pGAPfucO-aldA Strain and Escherichia coli MG1655/pGAPfucO Strain The Escherichia coli MG1655/pGAPfucO-aldA strain obtained in Example 2 and the Escherichia coli MG1655/pGAPfucO strain obtained in Example 1 were cultured in the same manner as in Example 3. However, the culture was carried out with the glucose amount of 70 g/L in the medium composition shown in Table 1. After culturing for 24 hours, the entire culture broth was collected by centrifugation to measure the weight of wet microbial mass obtained. Furthermore, the amount of residual glucose in the medium was measured according to an established method and the amount of glucose necessary for growth of the microbial mass was calculated. The results are shown in Table 3.

Even though the weights of microbial mass obtained from these two strains were almost the same, it was shown that the amount of glucose which was needed at that time could be 20% or more less in the MG1655/pGAPfucO-aldA strain. It was shown that lactaldehyde dehydrogenase was not necessarily needed in the production of glycolic acid in Example 7, but it was confirmed that lactaldehyde dehydrogenase was effective in the reduction of the amount of glucose necessary for the production of glycolic acid due to the enhanced activity of the enzyme.

TABLE 3

|  | MG1655/pGAPfucO strain | MG1655/pGAPfucO-aldA strain |
|---|---|---|
| Weight of wet microbial mass (g) | 45.3 | 45.5 |
| Consumption of glucose (g) | 31.6 | 24.5 |

Example 9

Substitution of the fucO Promoter on the Genome of Escherichia coli MG1655 Strain with GAPDH Promoter The entire base sequence of the genome DNA of Escherichia coli is known (GenBank accession number: U00096), and the base sequence of fucO of Escherichia coli has also been reported (GenBank accession number: M31059). PCR was performed using GCTCTAGACCTTCTCCTTGT-TGCTTTACG (Sequence No. 12) and AACTGCA-GAGAGAGGTAGCTAATGGAACG (Sequence No. 13), which were prepared on the basis of the gene information of 5'-adjacent region of fucO of the Escherichia coli MG1655 strain, using the genome DNA of Escherichia coli as a template, to amplify a DNA fragment of about 650 bp.

Furthermore, PCR was performed using GGTCTAGAG-CAATGATTGACACGATTCG (Sequence No. 14) which was prepared on the basis of the sequence information of glyceraldehyde 3-phosphate dehydrogenase (GAPDH) promoter of the Escherichia coli MG1655 strain, and CAGG-TACCATCCTTATCACCAGCAACC (Sequence No. 15) which was prepared on the basis of the sequence information of fucO of the Escherichia coli MG1655 strain, using the expression vector pGAPfucO prepared in Example 1 as a template, to give a DNA fragment of about 730 bp which contains a GAPDH promoter and an initiation codon-adjacent region of fucO.

Each of the fragments obtained above was digested with restriction enzymes PstI and XbaI, and XbaI and KpnI, and this fragment was mixed with the fragment obtained by digestion of temperature-sensitive plasmid pTH18cs1 (GenBank accession number: AB019610) [Hashimoto-Gotoh, T., Gene, Vol. 241, pp. 185-191 (2000)] with PstI and KpnI, ligated using a ligase, and then transformed to a DH5 strain at 30 degree centigrade, to give a transformant which grows on an LB agar plate containing 10 µg/ml of chloramphenicol. The obtained colony was cultured in an LB liquid medium containing 10 µg/ml of chloramphenicol at 30 degree centigrade overnight, and a plasmid was recovered from the obtained microbial mass. This plasmid was transformed to a MG1655 strain at 30 degree centigrade, and cultured on an LB agar plate containing 10 µg/ml of chloramphenicol at 30 degree centigrade overnight to give a transformant. The obtained transformant was applied onto an LB liquid medium containing 10 µg/ml of chloramphenicol and cultured at 30 degree centigrade overnight. Next, in order to obtain the cultured microbial mass, the cultured microbial mass was applied onto an LB agar plate containing 10 µg/ml of chloramphenicol to give colonies which grow at 42 degree centigrade. The obtained colonies were cultured in an LB liquid medium without containing an antibiotic at 30 degree centigrade overnight and further applied onto an LB agar plate without containing an antibiotic to give colonies which grow at 42 degree centigrade.

From the grown colonies, 100 colonies were picked up randomly, and each of them was grown on an LB agar plate without containing an antibiotic and an LB agar plate containing 10 µg/ml of chloramphenicol, to select chloramphenicol-sensitive clones. Furthermore, a fragment of about 730 bp containing a GAPDH promoter and a fucO partial sequence was amplified by PCR using the chromosome DNA of these desired clones, to select a strain in which the fucO promoter region is substituted with the GAPDH promoter, and the clone which satisfies the above description was named as an MG1655fucO-deleted GAPpfucO genome-inserted strain.

Example 10

Production of Glycolic Acid by MG1655fucO-Deleted GAPpfucO Genome-Inserted Strain The Escherichia coli MG1655fucO-deleted GAPpfucO genome-inserted strain was cultured, collected and washed in the same manner as in Example 3, and then ethylene glycol was added to the obtained microbial mass in the same manner as in Example 3 to carry out the reaction for 24 hours. Accumulation of glycolic acid was not confirmed.

Example 11

Construction of fucO Expression Vector Using a Low Copy Vector

PCR was performed using AACGAATTCTCGCAAT-GATTGACACGATTC (Sequence No. 3) which was prepared on the basis of the sequence information of the glyceraldehyde 3-phosphate dehydrogenase (GAPDH) promoter of the *Escherichia coli* MG1655 strain and GTGAAGCTTG-CATTTACCAGGCGGTATGG (Sequence No. 2) which was prepared on the basis of the sequence information of fucO of the *Escherichia coli* MG1655 strain, using the expression vector pGAPfucO prepared in Example 1 as a template, to give a DNA fragment of about 1,300 bp which contains a GAPDH promoter and fucO.

The DNA fragment was mixed with the fragment obtained by digestion of plasmid pACYC184 (GenBank accession number: X06403) with a restriction enzyme HincII, ligated using a ligase, and then transformed to an *Escherichia coli* DH5 strain, to give a transformant which grows on an LB liquid containing 20 μg/mL of chloramphenicol. The obtained colony was cultured in an LB liquid medium containing 20 μg/mL of chloramphenicol at 37 degree centigrade overnight, and a plasmid pACYCfucO was recovered from the obtained microbial mass. This plasmid pACYCfucO was transformed to an *Escherichia coli* MG1655 strain, and cultured in an LB agar plate containing 20 μg/mL of chloramphenicol at 37 degree centigrade overnight to give a MG1655/pACYCfucO strain.

Example 12

Production of Glycolic Acid by MG1655/pACYCfucO Strain

An *Escherichia coli* MG1655/pACYCfucO strain was cultured, collected and washed in the same manner as in Example 3, and then ethylene glycol was added to the obtained microbial mass in the same manner as in Example 3 to carry out the reaction for 9 hours. 28 g of glycolic acid was accumulated by the reaction.

Example 13

Measurement of Activity of Lactaldehyde Reductase of MG1655 Wild Strain, MG1655fucO-deleted GAPpfucO genome-inserted strain, MG1655/pACYCfucO Strain and MG1655/pGAPfucO Strain Each of microbial masses was cultured in the same manner as in Example 3. The microbial mass after the culture was collected and washed, and then suspended with pH 7.4 of 50 mM potassium phosphate buffer solution and disrupted with ultrasonic waves. The microbial mass extract after disruption was centrifuged and the supernatant was used for the measurement of activity of lactaldehyde reductase. Ethylene glycol was used as a substrate and the increase in reduced nicotinamide adenine dinucleotide produced by the reaction was measured using a spectrophotometer to measure the activity. The amount of reduced nicotinamide adenine dinucleotide generated for a minute per weight of a soluble protein used for the reaction was calculated, and the results are shown in Table 4 when the value of the MG1655 wild strain was 1.

In the MG1655fucO-deleted GAPpfucO genome-inserted strain, activity of lactaldehyde reductase was considerably increased to 18 times of the MG1655 wild strain. However, it was shown that such an increase in activity was not sufficient for the production of glycolic acid, and the increase in activity of at least about 1,700 times was needed as indicated by the case where the activity was enhanced by the introduction of a low copy vector for the production of glycolic acid due to the sole enhancement of lactaldehyde reductase.

TABLE 4

|  | MG1655 wild strain | MG1655fucO-deleted GAPpfucO genome-inserted strain | MG1655/pACYCfucO strain | MG1655/pGAPfucO strain |
|---|---|---|---|---|
| Relative activity of lactaldehyde reductase | 1 | 18.3 | 1783.7 | 3724.1 |

Example 14

Production of L-Glyceric Acid by *Escherichia coli* MG1655/pGAPfucO Strain and *Escherichia coli* MG1655 Wild Strain

*Escherichia coli* MG1655/pGAPfucO strain and *Escherichia coli* MG1655 wild strain were cultured, collected and washed in the same manner as in Example 3, and then glycerol was added instead of ethylene glycol added in Example 3 to the obtained microbial mass in a lump so as to have its concentration of 150 g/L to carry out the reaction for 24 hours with 500 ml of final liquid amount. The amount of L-glyceric acid accumulated in the obtained culture broth was measured by HPLC using a column for resolving optical isomers according to an established method. In the *Escherichia coli* MG1655/pGAPfucO strain, accumulation of 67 g/L of L-glyceric acid was confirmed at 24 hours. In the *Escherichia coli* MG1655 wild strain, accumulation of L-glyceric acid was not confirmed.

Example 15

Production of Hydroxyethoxy Acetate by *Escherichia coli* MG1655/pGAPfucO Strain and *Escherichia coli* MG1655 Wild Strain

*Escherichia coli* MG1655/pGAPfucO strain and *Escherichia coli* MG1655 wild strain were cultured in the same manner as in Example 3. The microbial mass at 24 hours after starting the culture was collected by centrifugation (8,000 rpm for 20 minutes) and washed with pH 7.2 of 1 mM potassium phosphate buffer solution. About 300 mg of the microbial mass after washing was suspended with the same buffer solution, and the reaction was carried out for 18 hours with 4 ml of final liquid amount in the presence of diethylene glycol in a final concentration of 100 mM. The reaction was carried out while stirring using a magnetic stirrer under atmospheric pressure at a reaction temperature of 37 degree centigrade. Hydroxyethoxy acetate in the obtained reaction solution was measured with HPLC according to an established method. In the *Escherichia coli* MG1655/pGAPfucO strain, accumulation of 1 g/L of hydroxyethoxy acetate was confirmed. Diethylene glycol-derived by-product including diglycolic acid was not detected. Furthermore, in the *Escherichia coli* MG1655 wild strain, accumulation of hydroxyethoxy acetate was not confirmed.

Example 16

Preparation of *Escherichia coli* MG1655glcDEF Gene-Deleted Strain

The entire base sequence of the genome DNA of *Escherichia coli* is known (GenBank accession number: U00096), and the base sequence of the glcDEF gene of *Escherichia coli* has been already reported (GenBank accession number: L43490). PCR was performed using the primer pair of TTGGTACCGTTCTGCCAGCAACTGACG (Sequence No. 16) and TGTCTAGAGTACCTCTGTGCGTCACTGG (Sequence No. 17), or the pair of GCTCTAGACGCTTTGTTGTGTTGTGTGG (Sequence No. 18) and AACTGCAGGATCGGTCAATGATTGCAGC (Sequence No. 19), which were prepared on the basis of the gene information of glcDEF gene-adjacent region of the genome DNA of *Escherichia coli* MG1655. Each of the obtained DNA fragments was digested with restriction enzymes KpnI and XbaI, and XbaI and PstI, to give fragments of about 670 bp and 790 bp respectively. These DNA fragments were mixed with the fragment obtained by digestion of a temperature-sensitive cloning vector pTH18cs1 (GenBank accession number: AB019610) [Hashimoto-Gotoh, T., Gene, Vol. 241, pp. 185-191 (2000)] with KpnI and PstI, ligated using a ligase, and then transformed to a DH5 strain at 30 degree centigrade, to give a transformant which grows on an LB agar plate containing 10 µg/ml of chloramphenicol. The obtained colony was cultured in an LB liquid medium containing 10 µg/ml of chloramphenicol at 30 degree centigrade overnight, and a plasmid was recovered from the obtained microbial mass. This plasmid was named as pTHΔglcDEF.

This plasmid pTHΔglcDEF was transformed to an *Escherichia coli* MG1655 strain at 30 degree centigrade, and cultured on an LB agar plate containing 10 µg/ml of chloramphenicol at 30 degree centigrade overnight to give a transformant. The obtained transformant was applied onto an LB liquid medium containing 10 µg/ml of chloramphenicol, and cultured at 30 degree centigrade overnight. Next, in order to obtain the cultured microbial mass, the cultured microbial mass was applied onto an LB agar plate containing 10 µg/ml of chloramphenicol to give colonies which grow at 42 degree centigrade. The obtained colonies were cultured in an LB liquid medium without containing an antibiotic at 30 degree centigrade overnight, and further applied onto an LB agar plate without containing an antibiotic to give colonies which grow at 42 degree centigrade.

From the grown colonies, 100 colonies were picked up randomly, and each of them was grown on an LB agar plate without containing an antibiotic and an LB agar plate containing 10 µg/ml of chloramphenicol, to select chloramphenicol-sensitive clones which grow only on an LB agar plate without containing an antibiotic. Furthermore, a fragment of about 3.8 kb containing a glcDEF gene was amplified by PCR using the chromosome DNA of these desired clones, to select a strain in which the glcDEF gene region was deleted, and the obtained strain was named as an MG1655glcDEF gene-deleted strain (hereinafter may be simply referred to as a ΔglcDEF strain).

Example 17

Preparation of *Escherichia coli* MG1655pflB Gene-Deleted Strain

The entire base sequence of the pflB gene of *Escherichia coli* has been already reported (GenBank accession number: X08035). PCR was performed using the primer pair of GCACGAAAGCTTTGATTACG (Sequence No. 20) and TTATTGCATGCTTAGATTTGACTGAAATCG (Sequence No. 21), or the pair of TTATTGCATGCTTATTTACTGCGTACTTCG (Sequence No. 22) and AAGGCCTACGAAAAGCTGCAG (Sequence No. 23), which were prepared on the basis of the gene information of pflB gene-adjacent region of the chromosome DNA of MG1655 strain. Each of the obtained DNA fragments was digested with restriction enzymes HindIII and SphI, and SphI and PstI, to give fragments of about 1,770 bp and 1,340 bp respectively. These DNA fragments were mixed with the fragment obtained by digestion of a temperature-sensitive cloning vector pTH18cs1 (GenBank accession number: AB019610) [Hashimoto-Gotoh, T., Gene, Vol. 241, pp. 185-191 (2000)] with HindIII and PstI, ligated using a ligase, and then transformed to a DH5 strain at 30 degree centigrade, to give a transformant which grows on an LB agar plate containing 10 µg/ml of chloramphenicol. The obtained colony was cultured in an LB liquid medium containing 10 µg/ml of chloramphenicol at 30 degree centigrade overnight, and a plasmid was recovered from the obtained microbial mass. This plasmid was transformed to an *Escherichia coli* MG1655 strain at 30 degree centigrade, and cultured on an LB agar plate containing 10 µg/ml of chloramphenicol at 30 degree centigrade overnight to give a transformant. The obtained transformant was applied onto an LB liquid medium containing 10 µg/ml of chloramphenicol and cultured at 30 degree centigrade overnight. Next, in order to obtain the cultured microbial mass, the cultured microbial mass was applied onto an LB agar plate containing 10 µg/ml of chloramphenicol to give colonies which grow at 42 degree centigrade. The obtained colonies were cultured in an LB liquid medium without containing an antibiotic at 30 degree centigrade overnight and further applied onto an LB agar plate without containing an antibiotic to give colonies which grow at 42 degree centigrade.

From the grown colonies, 100 colonies were picked up randomly, and each of them was grown on an LB agar plate without containing a drug and an LB agar plate containing 10 µg/ml of chloramphenicol, to select chloramphenicol-sensitive clones which grow only on an LB agar plate without containing an antibiotic. Furthermore, a fragment of about 2.0 kb containing a pflB gene was amplified by PCR using the chromosome DNA of these desired clones, to select a strain in which the pflB gene region was deleted, and the obtained strain was named as an MG1655pflB gene-deleted strain (hereinafter may be simply referred to as ΔpflB strain).

Example 18

Preparation of *Escherichia coli* MG1655pflB&glcDEF Gene-Deleted Strain

The plasmid pTHΔglcDEF obtained in Example 16 was transformed to a ΔpflB strain to finally give an MG1655pflB&glcDEF gene-deleted strain (hereinafter may be simply referred to as a ΔpflBΔglcDEF strain). The detailed method was the same as that described in Example 16.

Example 19

Construction of ΔglcDEF/pGAPfucO Strain, ΔpflB/pGAPfucO Strain and ΔpflBΔglcDEF/pGAPfucO Strain The plasmid pGAPfucO obtained in Example 1 was transformed to the ΔglcDEF strain obtained in Example 16, ΔpflB strain obtained in Example 17 and ΔpflBΔglcDEF strain obtained in Example 18 respectively, and cultured on an LB agar plate containing 50 μg/mL of ampicillin at 37 degree centigrade overnight to give a ΔglcDEF/pGAPfucO strain, a ΔpflB/pGAPfucO strain and a ΔpflBΔglcDEF/pGAPfucO strain.

Example 20

Production of glycolic acid by ΔglcDEF/pGAPfucO strain, ΔpflB/pGAPfucO strain and ΔpflBΔglcDEF/pGAPfucO strain The MG1655/pGAPfucO strain obtained in Example 3, and ΔglcDEF/pGAPfucO strain, ΔpflB/pGAPfucO strain and ΔpflBΔglcDEF/pGAPfucO strain obtained in Example 19 were cultured in the same manner as in Example 3. The microbial mass at 24 hours after starting the culture was collected by centrifugation (8,000 rpm for 20 minutes) and washed with distilled water. 75 g of the microbial mass after washing was weighed and suspended with distilled water along with 150 g of ethylene glycol to have 1,500 ml of final liquid amount. The suspension was transferred to a culture apparatus of DPC-2 fermentor manufactured by ABLE Corporation to carry out the reaction for 22 hours. The reaction was carried out under the conditions including atmospheric pressure, an aeration rate of 0.7 vvm, a stirring speed of 800 rpm, a reaction temperature of 35 degree centigrade and pH 7.2 (adjusted with an aqueous $NH_3$ solution). The amount of glycolic acid, oxalic acid and acetic acid accumulated in the obtained reaction solution, and the residual amount of ethylene glycol were measured by HPLC according to an established method. The results are shown in Table 5. A by-product organic acid such as oxalic acid and acetic acid can be reduced by deletion of glcDEF gene and/or pflB gene, the conversion rate of ethylene glycol was improved, and the productivity of glycolic acid was dramatically improved.

TABLE 5

|  | MG1655/ pGAPfucO strain | ΔglcDEF/ pGAPfucO strain | ΔpflB/ pGAPfucO strain | ΔpflB ΔglcDEF/ pGAPfucO strain |
|---|---|---|---|---|
| Glycolic acid (g) | 102.0 | 180.2 | 176.7 | 179.4 |
| Ethylene glycol (g) | 60.5 | Not detected | 0.5 | Not detected |
| Oxalic acid (g) | 4.06 | 1.11 | 2.88 | 1.23 |
| Acetic acid (g) | 0.13 | 0.18 | 0.10 | 0.10 |

The invention claimed is:

1. A process for producing hydroxycarboxylic acids with aliphatic polyhydric alcohols having a terminal hydroxyl group as a substrate, which comprises:
reacting an aliphatic polyhydric alcohol having a terminal hydroxyl group with an *Escherichia coli* which has imparted or enhanced lactaldehyde reductase activity, thereby producing a hydroxycarboxylic acid, wherein:
said *Escherichia coli* comprises a plasmid comprising a gene encoding a lactaldehyde reductase,
said aliphatic polyhydric alcohol having a terminal hydroxyl group is ethylene glycol, diethylene glycol, or glycerol, wherein an endogenous glycolate oxidase and/or an endogenous pyruvate formate-lyase activity of said *Escherichia coli* is inactivated or decreased, and
further wherein the yield of said hydroxycarboxylic acid is not less than 95% and the production rate is not less than 2 g/L/hr.

2. The process as set forth in claim 1, wherein
said plasmid further comprises a gene encoding a lactaldehyde dehydrogenase.

3. The process as set forth in claim 1, wherein the hydroxycarboxylic acid is a hydroxycarboxylic acid having optical activity.

4. The process as set forth in claim 2, wherein the hydroxycarboxylic acid is a hydroxycarboxylic acid having optical activity.

5. A process for producing glycolic acid obtained by using ethylene glycol, the method comprising:
reacting ethylene glycol with an *Escherichia coli* which has imparted or enhanced lactaldehyde reductase activity, thereby producing glycolic acid, wherein:
said *Escherichia coli* comprises a plasmid comprising a gene encoding lactaldehyde reductase and wherein an endogenous glycolate oxidase and/or an endogenous pyruvate formate-lyase activity of said *Escherichia coli* is inactivated or decreased,
said gene encoding lactaldehyde reductase is functionally linked to a promoter of a glyceraldehyde 3-phosphate dehydrogenase gene, and
further wherein the yield of glycolic acid is not less than 95% and the production rate is not less than 2 g/L/hr.

6. The process as set forth in claim 1, wherein said aliphatic polyhydric alcohol having a terminal hydroxyl group is ethylene glycol, and said hydroxycarboxylic acid is glycolic acid.

7. The process as set forth in claim 2, wherein said aliphatic polyhydric alcohol having a terminal hydroxyl group is ethylene glycol, and said hydroxycarboxylic acid is glycolic acid.

8. The process as set forth in claim 1, wherein said gene encoding said lactaldehyde reductase is functionally linked to a promoter of a glyceraldehyde 3-phosphate dehydrogenase gene.

9. The process as set forth in claim 2, wherein said gene encoding said lactaldehyde dehydrogenase and said gene encoding said lactaldehyde reductase are functionally linked to a promoter of a glyceraldehyde 3-phosphate dehydrogenase gene.

10. The process as set forth in claim 1, wherein said aliphatic polyhydric alcohol having a terminal hydroxy group is ethylene glycol.

* * * * *